United States Patent [19]

Staffier et al.

[11] 3,996,346
[45] Dec. 7, 1976

[54] COMPOSITION FOR REDUCING BODILY ODOR AND PERSPIRATION

[76] Inventors: Dominic Thomas Staffier, 19 Breed St., East Boston, Mass. 02128; Samuel Louis Shershow, 72 Lancaster Ave., Revere, Mass. 02151; William Barry Norton, 85 Longmeadow Road, Norwood, Mass. 02062

[22] Filed: Mar. 18, 1975

[21] Appl. No.: 559,548

[52] U.S. Cl. .................................. 424/67; 424/47
[51] Int. Cl.² ...................................... A61K 7/36
[58] Field of Search .................. 424/65, 45, 67; 260/429.9

[56] References Cited

UNITED STATES PATENTS

| | | | |
|---|---|---|---|
| 1,994,002 | 3/1935 | Mills | 260/429.9 H |
| 2,125,961 | 9/1938 | Shoemaker | 260/429.9 X |
| 2,145,583 | 1/1939 | Carlson | 424/68 X |
| 2,226,177 | 12/1940 | Orelup et al. | 424/68 X |
| 3,493,650 | 2/1970 | Dunkel | 424/65 |

OTHER PUBLICATIONS

Goodman, Cosmetic Dermatology, 1936, pp. 60, 309, 286, 287, 292, 293, 506 to 511.
Pharmaceutical Formulas, 1944, vol. 2, pp. 78, 67, 66 and 89, 68 to 72.
Sagarin, Cosmetics Science & Technology, 1957, pp. 717 & 718.

*Primary Examiner*—Dale R. Ore
*Attorney, Agent, or Firm*—Morse, Altman, Oates & Bello

[57] ABSTRACT

Deodorant and antiperspirant compositions for topical use, particularly underarm and foot application, containing specific proportions of zinc oxide, phenol, glycerin and calcium hydroxide and methods for producing such compositions.

10 Claims, No Drawings

COMPOSITION FOR REDUCING BODILY ODOR AND PERSPIRATION

BACKGROUND OF THE INVENTION

1. Field of Invention

The present invention relates to compositions for reducing perspiration and bodily odor, and to methods for producing such compositions.

2. Description of the Prior Art

In preparations, such as solutions and creams, intended for the purpose of reducing perspiration at localized areas of the body, it has been customary to employ various metallic salts, for example, of zinc, iron and aluminum. Thus, use has been made of the chlorides and sulfates of zinc, iron and aluminum. Such metallic salts, which have been established to have some degree of effectiveness, have been found occasionally to cause local epidermal irritation. A need has arisen for a deodorant and antiperspirant composition which more effectively reduces perspiration and bodily odor with a lower incidence of epidermal irritation.

SUMMARY OF THE INVENTION

It is an object of the present invention to provide a method and composition which more effectively reduce perspiration and bodily odor while exhibiting low levels of skin toxicity and allergic sensitivity.

Another object of the present invention is to provide deodorant and antiperspirant compositions, particularly for underarm and foot application, consisting essentially of specific proportions of zinc oxide, phenol, glycerin and calcium hydroxide and a method for producing such compositions.

These and other objects of the present invention will in part be obvious and will in part appear in the ensuing disclosure.

The invention accordingly comprises the processes and products, together with their steps, elements and interrelationships that are exemplified in the following disclosure, the scope of which will be indicated in the appended claims.

DETAILED DESCRIPTION OF THE PREFERRED EMBODIMENTS

In accordance with the present invention, it has been found that a composition consisting essentially of 100 to 500 parts powdered zinc oxide, 1 to 5 parts liquid phenol, 30 to 180 parts glycerin and 15 to 90 parts calcium hydroxide effectively reduces perspiration and bodily odor, exhibits low toxicity levels and is generally non-allergic. Such a composition defines a synergistic combination characterized by highly effective antiseptic and astringent properties. That is, the composition provides a degree of antiseptic and astringent activity which is more efficacious than the antiseptic and astringent activity of the compounds taken independently.

The zinc oxide-$Z_nO_2$, an astringent, and the liquid phenol-$C_6H_5OH$, an antiseptic, react to form zinc phenate-$Z_n(C_6H_5OH)_2$. The glycerin-$CH_2OH.CHOH.CH_2OH$-is operative as an emollient, humectant and antiseptic. The calcium hydroxide-$Ca(OH)_2$- is operative as a protective astringent.

One embodiment of the invention, a deodorant and antiperspirant cream, consists essentially of:

a. from about 12 percent to about 50 percent by total weight of powdered zinc oxide;

b. from about 0.1 percent to about 0.4 percent by total weight of liquid phenol;

c. from about 3 percent to about 18 percent by total weight of glycerin;

d. from about 0.1 percent to about 9 percent by total weight of calcium hydroxide (lime water); and e. from about 30 percent to about 94 percent by total weight of a vehicle, for example a vanishing cream such as a stearate cream. The especially preferred limits of the vanishing cream is from about 50 percent to about 75 percent.

The following two examples are presented to illustrate various vanishing creams used in the deodorant and antiperspirant composition embodying the invention, but is should be understood that such examples are not intended as an exclusive teaching.

EXAMPLE I

| | |
|---|---|
| Stearic Acid | 18 lb. |
| Glycerin | 6 pints |
| Ammonia Water 26° Baume | 1 pint 2 oz. |
| Water | 11 gal. |
| Perfume | |

Stearic acid is melted at low heat. The glycerin is mixed with ammonia and 11 gal. of water. The stearic acid is added in several portions, heating and stirring until a smooth and liquid intermediate composition is formed. When all water has been added, the intermediate composition is removed from the heat and the perfume is added. The composition is stirred occassionally until cold and then strained through cheese cloth to form a final composition.

EXAMPLE II

| | | |
|---|---|---|
| Stearic Acid | 16 | lb. |
| Water | 74 | lb. |
| Glycerin | 10 | lb. |
| Borax | 1.5 | lb. |
| Potassium Carbonate | 0.5 | lb. |
| Glycerin | 5 | lb. |
| Perfume | | |

The stearic acid and glycerin are melted on a water bath at 70° C. The potassium carbonate and borax are dissolved in water at 70° C. This solution is added very slowly, constantly stirring, to stearic acid and glycerin, the heat having been turned off. After all water is added, the solution is stirred until cream forms. Then, the heat is turned on again and is stirred until the composition is practically liquid. The heat is turned off and the composition is stirred until cold. Shortly before the composition is cool, the glycerin is added. The following example III is illustrative of a deodorant and antiperspirant composition embodying the present invention.

EXAMPLE III

| | Parts |
|---|---|
| Powdered zinc oxide USP | 25 |
| Liquefied phenol USP | 0.25 |
| Glycerin USP | 9 |
| Calcium hydroxide | 3 |
| Vanishing cream | 62.5 |
| Yellow food coloring | 0.25 |

Example III-continued

| | Parts |
|---|---|
| Red food coloring | 0.25 |

The yellow food coloring and the red food coloring are added for aesthetic purposes. The range of the food coloring is from about 0.1 parts to 0.9 parts.

The composition recited in the foregoing Example III was prepared by hand using a pestle and mortar. First, four ounces of vanishing cream was placed in the mortar. Next, five minims of liquid phenol, three fluidrams of glycerin, one fluidram of calcium hydroxide, four minims of yellow food coloring and four minims of red food coloring were poured into and mixed in separate containers to form an intermediate mixture. Next, the intermediate mixture was poured into the mortar and blended with the vanishing cream to form an intermediate composition. Next, one ounce of powdered zinc oxide was placed in the mortar. Finally, using the pestle, the zinc oxide and intermediate composition were levigated thoroughly to form a final composition.

The final composition given in Example III efficaciously reduces perspiration and bodily odor, while exhibiting low toxicity levels. Such a composition, which is applied sparingly, has been found to be very effective in reducing underarm odor and perspiration as well as foot odor and perspiration without causing epidermal irritation or allergic reaction. Generally, the composition is applied sparingly to the underarm and/or foot area and is rubbed until it vanishes. In certain cases, underarm odor and perspiration have been controlled effectively for approximately 1 to 2 days. In certain other cases in which the composition has been applied between the toes and foot bottom, control of foot odor and perspiration have been effective for approximately 7 to 10 days.

In an alternative embodiment, the antiperspirant and deodorant composition is in the form of a spray or a roll-on. In the case of a spray, any liquefiable propellant can be used as a vehicle in the compositions of this invention. Examples of materials that are suitable for use as propellants are trichlorofluoromethane, dichlorodifluoromethane, dichloratetrafluoroethane, monochlorodifluoromethane, trichlorotrifluoroethane, propane, butane, and isobutane, used singly or admixed. Trichlorofluoromethane, dichlorodifluoromethane, dichlorotetrafluoroethane, and isobutane, used singly or admixed, are preferred.

The amount of the propellant gas is governed by normal factors as well known in the aerosol art. It is satisfactory to consider the propellant as constituting the balance of the composition of the instant invention that is not accounted by the other components as detailed herein. The preferred limits of propellant are therefore from about 70.0 percent to about 93.9 percent. Especially preferred limits are from about 80 percent to about 92 percent.

The following example illustrates a spray embodying the invention, percentages being by total weight.

EXAMPLE IV

| Zinc oxide | 25 percent |
|---|---|
| Phenol | 0.25 percent |
| Glycerin | 9 percent |
| Calcium hydroxide | 3 percent | and the balance being a propellant mixture comprising 60 percent trichlorofluoromethane and 40 percent dichlorodifluoromethane.

The following example illustrates a roll-on embodying the invention, percentages by total weight.

EXAMPLE V

| Zinc oxide | 25 percent |
|---|---|
| Phenol | 0.25 percent |
| Glycerin | 9 percent |
| Calcium hydroxide | 3 percent |
| Water soluble lanolin | 62.75 percent |

Since certain changes may be made in the foregoing disclosure without departing from the scope of the invention herein involved, it is intended that all matter contained in the above description be construed in an illustrative and not in a limiting sense.

What is claimed is:
1. A deodorant and antiperspirant composition in the form of a cream consisting essentially of:
   a. from about 12 percent to about 50 percent by total weight of zinc oxide;
   b. from about 0.1 percent to about 0.4 percent by total weight of phenol;
   c. from about 3 percent to about 18 percent by total weight of glycerin;
   d. from about 0.1 percent to about 9 percent by total weight of calcium hydroxide; and
   e. from about 30 percent to 94 percent by total weight of a cream base;
   f. predetermined proportions of said zinc oxide and said phenol being combined in the form of zinc phenate;
   g. said zinc oxide, phenol, glycerin and calcium hydroxide characterizing a deodorant and antiperspirant composition, said cream base constituting a vehicle for applying said composition to selected portions of the body.

2. The composition as claimed in claim 1 wherein said cream base is a stearic acid vanishing cream.

3. The composition as claimed in claim 2 wherein the percent by total weight of said stearic acid vanishing cream is approximately 62.5 percent.

4. The composition as claimed in claim 1 wherein the percent by total weight of said zinc oxide is approximately 25 percent.

5. The composition as claimed in claim 4 wherein the percent by total weight of said phenol is approximately 0.25 percent.

6. The composition as claimed in claim 5 wherein the percent by total weight of said glycerin is approximately 9 percent.

7. The composition as claimed in claim 6 wherein the percentage by weight of said calcium hydroxide is approximately 3 percent.

8. A deodorant and antiperspirant composition in the form of a cream consisting essentially of:
   a. approximately 25 parts of powdered zinc oxide;
   b. approximately 0.25 parts liquefied phenol;
   c. approximately 9 parts glycerin;
   d. approximately 3 parts calcium hydroxide;
   e. approximately 62.5 parts vanishing cream; and f. approximately 0.5 parts food coloring;

g. predetermined proportions of said powdered zinc oxide and said liquefied phenol combining in the form of zinc phenate;

h. said zinc oxide, phenol, glycerin and calcium hydroxide characterizing a deodorant and antiperspirant composition, said cream base constituting a vehicle for applying said composition to selected portions of the body.

9. A method for forming a deodorant and antiperspirant composition in the form of a cream, said method comprising the steps of:

a. placing from about 50 percent to about 75 percent by total weight of vanishing cream in a container;

b. preparing an intermediate mixture consisting essentially of from about 0.1 percent to about 0.4 percent by total weight of liquefied phenol, from about 3 percent to about 18 percent by total weight or glycerin, and from about 0.1 percent to about 9 percent by total weight of calcium hydroxide;

c. pouring said intermediate mixture into said containers;

d. blending said intermediate mixture and said vanishing cream to form an intermediate composition;

e. adding from about 12 percent to about 50 percent by total weight of powdered zinc oxide; and f. levigating said intermediate composition and said powdered zinc oxide to form a final composition, predetermined portions of said powdered zinc oxide and said liquefied phenol combining in the form of zinc phenate in said final composition.

10. The method as claimed in claim 9 wherein said vanishing cream is a stearic acid cream.

* * * * *